United States Patent
Sauer et al.

(10) Patent No.: US 8,218,715 B2
(45) Date of Patent: Jul. 10, 2012

(54) METHODS AND SYSTEMS TO FACILITATE CORRECTING GAIN FLUCTUATIONS IN ITERATIVE IMAGE RECONSTRUCTION

(75) Inventors: Ken David Sauer, South Bend, IN (US); Charles Addison Bouman, West Lafayette, IN (US); Jiang Hsieh, Brookfield, WI (US); Jean-Baptiste Thibault, Milwaukee, WI (US)

(73) Assignees: General Electric Company, Schenectady, NY (US); Purdue Research Foundation, West Lafayette, IN (US); The University of Notre Dame du Lac, Notre Dame, IN (US)

(*) Notice: Subject to any disclaimer, the term of this patent is extended or adjusted under 35 U.S.C. 154(b) by 114 days.

(21) Appl. No.: 12/602,194

(22) PCT Filed: May 31, 2007

(86) PCT No.: PCT/US2007/070124
§ 371 (c)(1),
(2), (4) Date: Apr. 6, 2010

(87) PCT Pub. No.: WO2008/147416
PCT Pub. Date: Dec. 4, 2008

(65) Prior Publication Data
US 2010/0215140 A1    Aug. 26, 2010

(51) Int. Cl.
*A61B 6/00* (2006.01)
(52) U.S. Cl. .............. 378/4; 378/207; 382/131
(58) Field of Classification Search .............. 378/4, 207; 382/131
See application file for complete search history.

(56) References Cited

U.S. PATENT DOCUMENTS

| | | | | |
|---|---|---|---|---|
| 4,135,247 | A * | 1/1979 | Gordon et al. | 378/11 |
| 4,789,930 | A * | 12/1988 | Sones et al. | 378/207 |
| 4,891,829 | A | 1/1990 | Deckman et al. | |
| 5,220,589 | A | 6/1993 | Gard | |
| 5,828,719 | A | 10/1998 | He et al. | |
| 5,974,113 | A * | 10/1999 | Bruijns et al. | 378/98.7 |
| 6,393,098 | B1 * | 5/2002 | Albagli | 378/98.2 |
| 6,411,673 | B1 * | 6/2002 | Bromberg et al. | 378/19 |
| 6,426,988 | B2 | 7/2002 | Yamada et al. | |
| 6,819,734 | B2 | 11/2004 | Raupach | |
| 7,042,974 | B2 * | 5/2006 | Goodgame et al. | 378/4 |
| 7,440,535 | B2 * | 10/2008 | Netsch et al. | 378/4 |
| 7,817,839 | B2 * | 10/2010 | Chen et al. | 382/132 |
| 7,876,944 | B2 * | 1/2011 | Stalling et al. | 382/128 |
| 2003/0103595 | A1 | 6/2003 | Raupach | |

(Continued)

FOREIGN PATENT DOCUMENTS
JP    63308548    12/1988
(Continued)

OTHER PUBLICATIONS

Zhang et al., Experimental Evaluation for Joint Estimation Approach, Department of Radiology, IEEE, 1997, pp. 1623-1627.*

(Continued)

*Primary Examiner* — Alexander H Taningco
(74) *Attorney, Agent, or Firm* — Armstrong Teasdale LLP (57) ABSTRACT

Methods and systems for reconstructing an image are provided. The method includes performing a tomographic image reconstruction using a joint estimation of at least one of a gain parameter and an offset parameter, and an estimation of the reconstructed image.

35 Claims, 5 Drawing Sheets

U.S. PATENT DOCUMENTS

| | | |
|---|---|---|
| 2005/0031069 A1 | 2/2005 | Kaucic et al. |
| 2005/0105693 A1 | 5/2005 | Zhao et al. |
| 2006/0011853 A1 | 1/2006 | Spartiotis et al. |
| 2006/0071174 A1 | 4/2006 | Spartiotis et al. |
| 2006/0072801 A1 | 4/2006 | Bernard Deman et al. |
| 2008/0043900 A1* | 2/2008 | Baba et al. ............ 378/4 |
| 2008/0063135 A1* | 3/2008 | DeMan et al. ............ 378/4 |
| 2009/0185655 A1 | 7/2009 | Koken et al. |

FOREIGN PATENT DOCUMENTS

| | | | |
|---|---|---|---|
| JP | 5168620 | A | 7/1993 |
| JP | 7191962 | A | 7/1995 |
| JP | 2001286463 | A | 10/2001 |
| JP | 2003153891 | A | 5/2003 |
| JP | 2003529423 | A | 10/2003 |
| WO | 0175793 | A2 | 10/2001 |
| WO | 2006003487 | A1 | 1/2006 |
| WO | 2006038145 | A1 | 4/2006 |

OTHER PUBLICATIONS

Elbakri et al., Statistical Image Reconstruction for Polyenergetic X-ray Computed Tomography, IEEE Transactions on Medical Imaging, vol. 21, No. 2, Feb. 2002, pp. 89-99.*

An International Search Report for copending international application PCT/US07/70124 (3 pages).

Japanese language Office Action, dated Apr. 10, 2012, for co-pending JP patent application No. 2010-510274 (4 pages).

An English language translation of JP Office Action, dated Apr. 10, 2012, for co-pending application No. 2010-510274 (7 pages).

An English language machine translation of JP 05-168620 (10 pages).

* cited by examiner

METHODS AND SYSTEMS TO FACILITATE CORRECTING GAIN FLUCTUATIONS IN ITERATIVE IMAGE RECONSTRUCTION

BACKGROUND OF THE INVENTION

This invention relates generally to tomographic imaging and more particularly, to reducing gain fluctuation in image reconstruction.

Imaging technology, for example, but not limited to computed tomographic (CT) scanning technology permits a non-invasive technique to obtain internal images of the human body for medical diagnostic purposes. In clinical practice, it is common for CT scans to results in data sets with truncated projections. Data truncation occurs when the patient, the CT table, or anything else placed in the bore of the scanner, extends beyond the scan field-of-view. This situation may arise for large patients, or when centering the desired patient anatomy at the center of the field-of-view. Even in situations where both the patient and the table are carefully positioned within the scan field-of-view, the table slicker often used to protect the CT table mechanism from bodily fluids may be left hanging off the sides of the table, and may extend outside the scan field of view. It is also possible for tubes of contrast liquid, intravenous (IV) fluids, or other medical accessories to be present outside the scan field-of-view.

CT imaging generally includes data acquisition, followed by a sequence of pre-processing corrections, before image reconstruction is performed to generate the patient images. Raw projection data is processed prior to image reconstruction by applying scanner-specific corrections and calibrations. One of the first steps is the reference normalization step, which addresses the impact of fluctuations in the x-ray tube current output on the projections. For this purpose, a set of reference channels is placed slightly outside the scan field-of-view, to measure x-ray photons directly from the x-ray tube without attenuation by the scanned object. Coefficients calculated from these channels monitor the x-ray flux and are used to normalize the projections relative to one another. When an object is present outside the scan field-of-view, however, the reference channels are blocked, and pre-processing cannot accurately estimate the correction coefficients. This and other steps in pre-correction modify the acquired projection data and may result in inaccurate projection measurements resulting in image artifacts.

Other sources of error may be present that could also result in a view dependent DC bias in the pre-processed data. For example, the gain of the detector cell can be angularly dependent as a result of the gravitational force on the collimator plates, which leads to variations in the shadow generated by these plates.

Image reconstruction denotes the process of generating images from the pre-corrected projection data. In practice, analytic techniques such as the Filtered Back-Projection algorithm (FBP) are typically used. Iterative reconstruction (IR) algorithms have also been more recently introduced for CT and offer the potential for significantly improved image quality over conventional FBP and other direct techniques. Pre-processing corrections and calibrations are tuned to minimize image artifacts for FBP-like algorithms and reconstruct an accurate map of CT numbers. However, using the same pre-processed data to initialize iterative reconstruction may result in significant image artifacts in cases where projection data is truncated.

BRIEF DESCRIPTION OF THE INVENTION

In one embodiment, a method of reconstructing an image includes performing a tomographic image reconstruction using a joint estimation of at least one of a gain parameter and an offset parameter, and an estimation of the reconstructed image.

In another embodiment, a Computed Tomography (CT) System includes an X-ray source, a radiation detector, and a computer coupled to the X-ray source and the radiation detector, the computer configured to perform an X-ray image reconstruction jointly using an estimation of error correction gain parameters and an estimation of the reconstructed image.

In yet another embodiment, a computer readable medium encoded with a program is configured to instruct a computer to iteratively reconstruct an X-ray image jointly using an estimation of error correction gain parameters and an estimation of the reconstructed image.

DETAILED DESCRIPTION OF THE INVENTION

In some known CT imaging system configurations, a radiation source projects a fan-shaped beam which is collimated to lie within an X-Y plane of a Cartesian coordinate system and generally referred to as an "imaging plane." The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

To further improve the data acquisition, a multi-slice or volumetric CT system may be utilized. Such systems collect multiple projections simultaneously by using a detector that includes a plurality of detector rows. In such configurations, the fan beam geometry becomes a cone beam geometry.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 1:
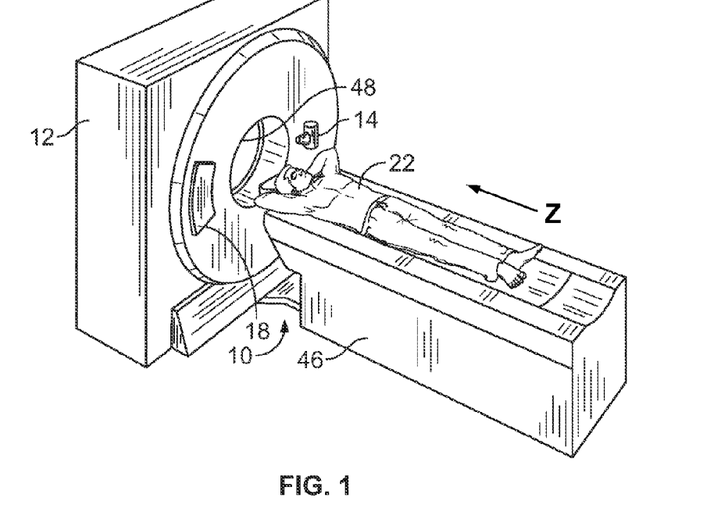
FIG. 1 is a pictorial view of a CT imaging system in accordance with an embodiment of the present invention.
Figure 2:
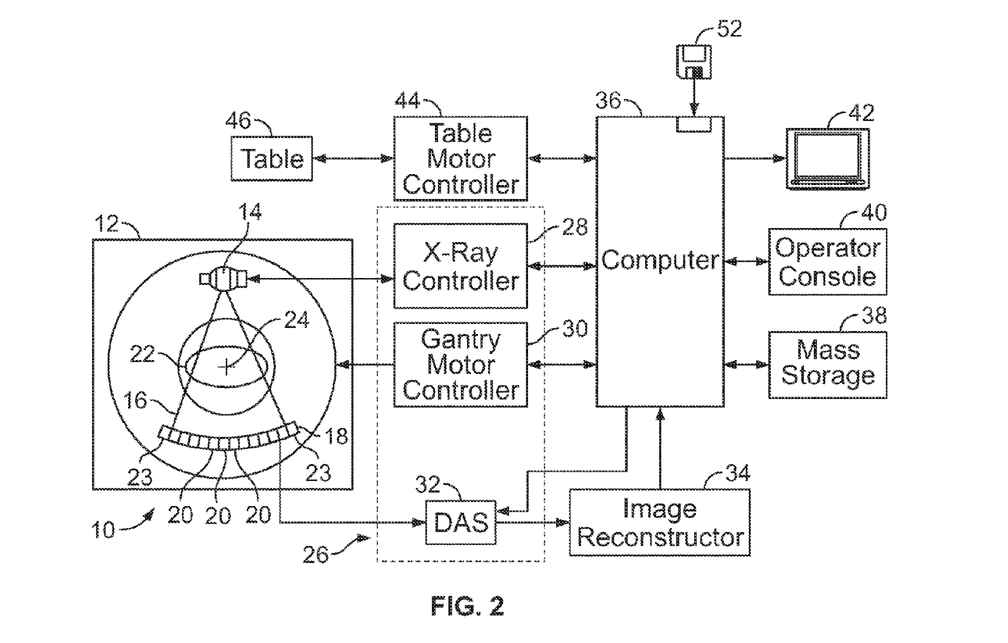
FIG. 2 is a block schematic diagram of the system illustrated in FIG. 1.

FIG. 1 is a pictorial view of a CT imaging system 10 in accordance with an embodiment of the present invention. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. Raw projection data is pre-processed prior to image reconstruction to reduce the impact of fluctuations in the x-ray tube current output on the projection data. A set of reference channels 23 is placed slightly outside cone beam 16, to measure x-ray photons directly from radiation source 14 without attenuation by object 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows. When object 22 is present outside cone beam 16, which defines the scan field-of-view, reference channels 23 are blocked, and pre-processing cannot accurately estimate the correction coefficients. Blockage of the reference channels and other gantry specific errors in pre-correction modify the acquired projection data and may result in inaccurate projection measurements resulting in image artifacts.

During a scan to acquire radiation projection data, gantry 12, and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the embodiments described herein are not limited to practice in CT system 10 and can be utilized in connection with many other types and variations of imaging systems. In one embodiment, computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, field programmable gate arrays (FPGA) and all other programmable circuits.

Herein described are new methods, apparatus, and software for accurate geometric forward modeling of third generation CT scanners that is suitable for iterative reconstruction of high quality clinical images for medical diagnostic purposes. The herein described methods support all configurations of CT scanners, including single-slice and multi-slice CT, as well as any trajectory of acquisition, such as step-and-shoot (axial) mode, helical mode, or any other mode, with constant or varying pitch and sampling patterns.

Traditionally, images have been reconstructed from computed tomography (CT) data using so-called direct reconstruction algorithms such as filtered back projection (FBP) or convolution back projection (CBP), for example. Recently, iterative reconstruction (IR) algorithms have been introduced for the reconstruction of CT images. One advantage of utilizing an iterative reconstruction algorithm is that the iterative reconstruction algorithm can more accurately model the measurements obtained from real CT systems. This is particularly true for helical CT systems that include multi-slice detectors because these systems produce projection measurements that pass obliquely through the 2-D reconstructed image planes. By more accurately modeling these projections, iterative reconstruction algorithms can generate images having higher quality, lower noise, and fewer artifacts.

For example, utilizing a helical scan CT system, the X-ray source and the detector array rotate around the object being scanned. If a helical CT scanner is utilized, then the X-ray source and detector also move in the direction perpendicular to the plane of rotation tracing out a generally helical path. At periodic moments in time, the detector array measures the X-ray energy that passes through the object. Each such measurement is known as a view. Generally, the detector array includes a plurality of detector elements that are arranged along the direction of rotation, referred to herein as channels. In addition, a multislice CT scanner also includes a plurality of rows. For example, a four slice detector includes four rows of detector elements, wherein each row includes a plurality of channels.

For a single rotation of the scanner, the detector measurements from the kth row of the detector are defined as $y_k = \{y_{ki}\}_{i=0}^{M-1}$, where M is the total number of measurements obtained from a single row of the detector in a single rotation, and $y_k$ is defined as a single slice of the data, and the entire set of data is defined as $y = \{y_k\}_{k=0}^{K_1-1}$, where $K_1$ is the number of slices in the detector.

Alternatively, $y_k$ may be a set of data, extracted from a plurality of detector rows in helical scans, which is used to construct an image on a conventional image plane, or a plane oblique to horizontal and/or vertical axes.

The volume being reconstructed is then discretized into voxels arranged along three dimensions, wherein the first two dimensions are generally oriented to be in the plane of rotation, and the third dimension is generally oriented perpendicularly, or approximately perpendicularly, to the plane of rotation. For example, $x_{ki}$ is defined as the voxel where k indexes the position along the third dimension and i indexes the specific voxel in the plane. Further, $x_k = \{x_{ki}\}_{i=0}^{N-1}$ is defined as the set of voxels in the kth plane, and the entire set of planes being reconstructed is defined as $x = \{x_k\}_{k=0}^{K_2-1}$, where $K_2$ is the number of planes in the volume.

Accordingly, the forward model for the scanner is the function which yields the expected measurement when forward projecting the images estimated by the reconstruction. More specifically, the forward model, F(x), is a function defined such that E[y]=F(x). In one embodiment, a simplifying approximation is made such that $E[y_k]=F(x_k)$.

Accordingly, and in the exemplary embodiment, an iterative reconstruction algorithm may be utilized to reconstruct an image utilizing a multislice CT reconstruction system. Iterative reconstruction algorithms are utilized to determine the unknown value of x by searching for the value of the vector x that best matches the measured data. In the exemplary embodiment, the mathematical formulation of the class of iterative reconstruction problems considered here takes the following general form in the counts domain:

$$\hat{x}, \hat{\alpha} = \underset{x,\alpha}{\operatorname{argmin}} F(y', Ax, \alpha), \text{ where} \quad (1)$$

F( ) represents a function of y', x, and α that penalizes deviations between observed measurements (y') and the estimated forward projections of x via the forward projection operator A, y' represents the raw measurements, x represents the unknown 3D image vector, α represents the vector of unknown multiplicative gain factors applied to the raw count measurements, and A represents the forward projection operator mapping the image space into the projection space.

An alternative general form in the projection domain is:

$$\hat{x}, \hat{\beta} = \underset{x,\beta}{\operatorname{argmin}} G(y, Ax, \beta), \text{ where} \quad (2)$$

G( ) represents a function of y, β, and Ax that penalizes deviations between observed measurements (y) and the estimated forward projections of x, y represents the vector of integral projection measurements, Ax represents a forward projection of the estimated object x through the forward projection operator A, and β is the vector of unknown additive offset factors applied to the integral projection measurements.

This equation represents the joint estimation of the image values in x and the gain parameters in β. β is a vector that represents the unknown additive offset in the projection domain by taking the log of unknown multiplicative gains $\alpha_i$ in the counts domain, per $\beta_i = \ln(\alpha_i)$. The $\beta_i$ are assumed fixed for any particular row and view, which guarantees that the number of parameters to be estimated for gain correction is small relative to the number of voxels in the 3D image.

Another generalization of this approach is the joint estimation of $\hat{x}$, $\hat{\alpha}$, and $\hat{\beta}$ using:

$$\hat{x}, \hat{\alpha}, \hat{\beta} = \underset{x,\alpha,\beta}{\operatorname{argmin}} G(y', y, Ax, \alpha, \beta) \quad (3)$$

In the exemplary embodiment, a specific embodiment is represented by:

$$\hat{x}, \hat{\beta} = \underset{x,\beta}{\operatorname{argmin}} G(y - (Ax + \beta)), \text{ where} \quad (4)$$

x is the vector of object coefficients to reconstruct from the vector of data measurements y, and the reconstruction problem is formulated as the minimization of a cost function G( ) applied to the difference between the measured data y and the vector of unknown additive offset factors β and a forward projection Ax of the estimated object x through the forward projection operator A. As described above, G( ) represents a function of (y−(Ax+β)) that penalizes deviations between observed measurements (y), and the unknown additive offset factors and the estimated forward projections of x. In other embodiments, G( ) represents a function of (y−Ax). The quantities (y−(Ax+β)) and (y−Ax) are referred to as "error sinograms" because they are the difference between the measured data and the expected data. The error sinogram is minimized in successive steps of the iterative algorithm chosen to solve the optimization problem. The reconstruction is improved by accounting for error from for example, but not limited to noise, an inaccurate reconstruction, and an inaccurate modeling of the scanner. In the exemplary embodiment, a weighted quadratic form for the cost function G( ) is selected. The optimization problem then becomes:

$$\hat{x}, \hat{\beta} = \underset{x,\beta}{\operatorname{argmin}}\{(y-(Ax+\beta))^T W(y-(Ax+\beta))\}, \text{ where} \quad (5)$$

$( )^T$ denotes the vector transpose operation, and W is a weighting matrix of confidence coefficients $w_i$ in the quality of the measurement data. Estimation of $\hat{x}$ above represents the solution of the Maximum Likelihood (ML) problem. Reconstruction may also be performed with the addition of an image model constraining the cost function as:

$$\hat{x}, \hat{\beta} = \underset{x,\beta}{\operatorname{argmin}}\{(y-(Ax+\beta))^T W(y-(Ax+\beta))+U(x)\} \text{ where} \quad (6)$$

U(x) is an image regularization term. In this case, estimation of $\hat{x}$, $\hat{\beta}$ represents the solution of the Maximum A Posteriori (MAP) problem.

Figure 3A:
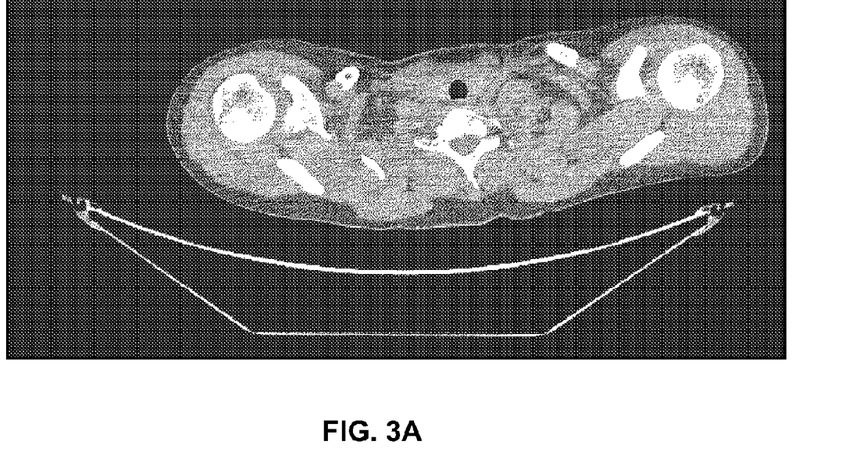
FIG. 3A is a FBP image of a human shoulder patient.
Figure 3B:
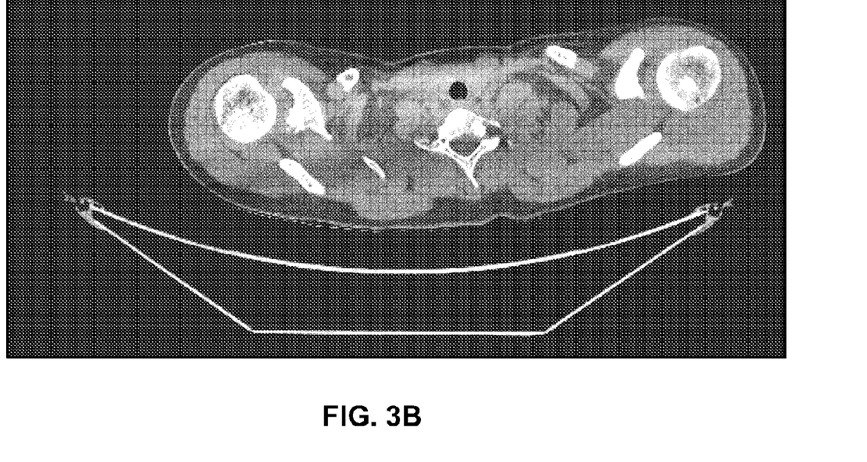
FIG. 3B is an uncorrected statistical iterative reconstruction image of the human shoulder patient.

FIG. 3A is a FBP image of a human shoulder patient. FIG. 3B is an uncorrected statistical iterative reconstruction image of the human shoulder patient. Low frequency shading artifacts 302 degrade the uncorrected IR image such that the image is not clinically acceptable. FIGS. 3A and 3B illustrate an example wherein an IR image may be degraded such that it is not clinically acceptable, while the FBP image does not exhibit the same artifacts. In this case, only the table slicker extends outside the scan field-of-view. The methods in accordance with embodiments of the present invention facilitate eliminating low-frequency truncation-related image artifacts in IR algorithms initialized from the same pre-processed projection data as generated for FBP.

Figure 4A:
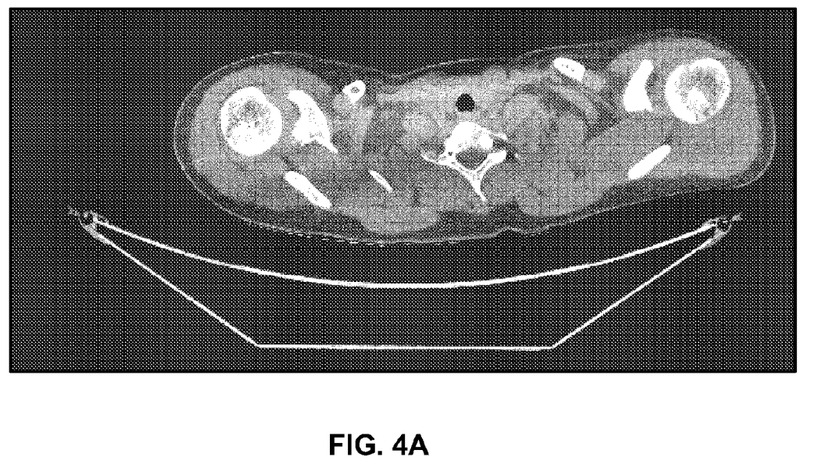
FIG. 4A is an uncorrected statistical iterative reconstruction image of the human shoulder patient shown in FIG. 3B.
Figure 4B:
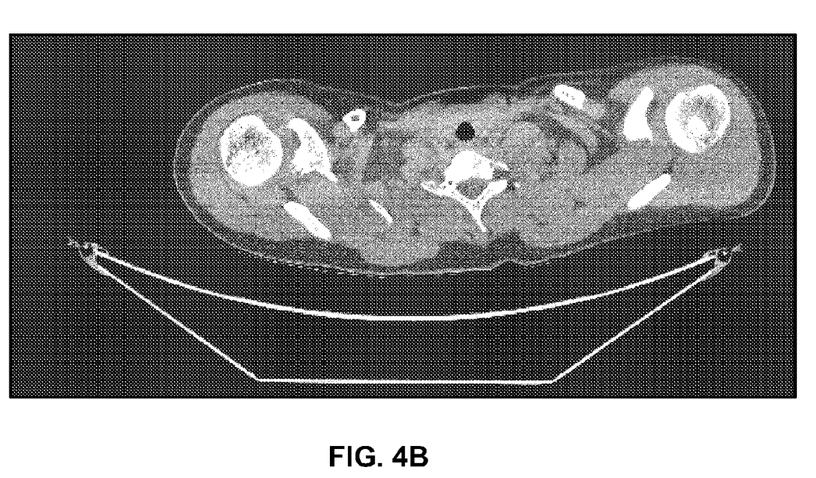
FIG. 4B is a statistical iterative reconstruction image of the human shoulder patient corrected by using the X-ray tube generator signal for reference normalization.

FIG. 4A is an uncorrected statistical iterative reconstruction image of the human shoulder patient (shown in FIG. 3B). FIG. 4B is a statistical iterative reconstruction image of the human shoulder patient corrected by using the X-ray tube generator signal rather than the true measured tube signal at the detector for reference normalization. A substantial reduction of low frequency shading in the iterative reconstruction image relative to the standard iterative reconstruction result using the X-ray tube generator signal for reference normalization.

Low-frequency shading artifacts 302 (shown in FIG. 3B) in iterative reconstruction images generally occur where projection data truncation exists. The root cause of the artifact for iterative reconstruction is related to an inaccurate estimation of the level of the signal for those projections that are truncated. For example, when the reference signal measured by reference channels 23 is blocked, the normalization coefficient calculated for the reference normalization step is inaccurate. As a result, the DC component of the signal is incorrect. For FBP-like algorithms, the impact of this problem is minimized by the presence of a ramp filter in the reconstruction steps. The ramp filter acts as a high-pass filter in the frequency domain and eliminates the DC component of the signal. Iterative reconstruction algorithms do not include a high-pass filter and instead consider the full frequency spectrum of the signal for reconstruction.

Some known reference normalization pre-processing uses the measured signal at the detector reference channels to compute the normalization coefficient. It is normally desirable to use the measured detector signal in order to account for variations in tube output flux that do not match the desired tube signal. However, when the measured signal is affected by something present between the tube and detector, or for any other reason, it may not provide a reliable estimation of the tube output, and the error introduced will likely generate artifacts in iterative reconstruction images.

In an embodiment, the sinogram data is normalized with the known X-ray tube generator signal, rather than reference channel measurements. In cases where reference channels are partially blocked, this signal contains fewer local, spurious oscillations and is therefore significantly more accurate as a normalization of the entire row of detector measurements than are the measured reference values.

In another embodiment, a method for artifact correction uses an initial condition with accurate low frequency content, but does not require changes in usual pre-processing prior to iterative reconstruction. The method is not limited in its ability to correct for actual gain fluctuation at the detector array.

A set of initial conditions that are used with this method is defined as an initial image volume where the low frequency information content accurately represents the scanned object. The FBP images resulting from FBP reconstruction of properly calibrated and corrected data represents a good set of initial conditions for some iterative algorithms, such as the Iterative Coordinate Descent (ICD) algorithm [5], or the Ordered Subsets (OS) algorithm [6]. The calibrations and other corrections applied during FBP-like (or more generally, any analytic, direct reconstruction technique) are designed to correctly render the low frequency information in the reconstructed volume. By starting from such initial conditions and conserving the low frequency content throughout the reconstruction, the iterative algorithms of the present embodiment facilitate producing a higher quality reconstruction of the scanned object, void of damaging low-frequency artifacts.

Figure 5:
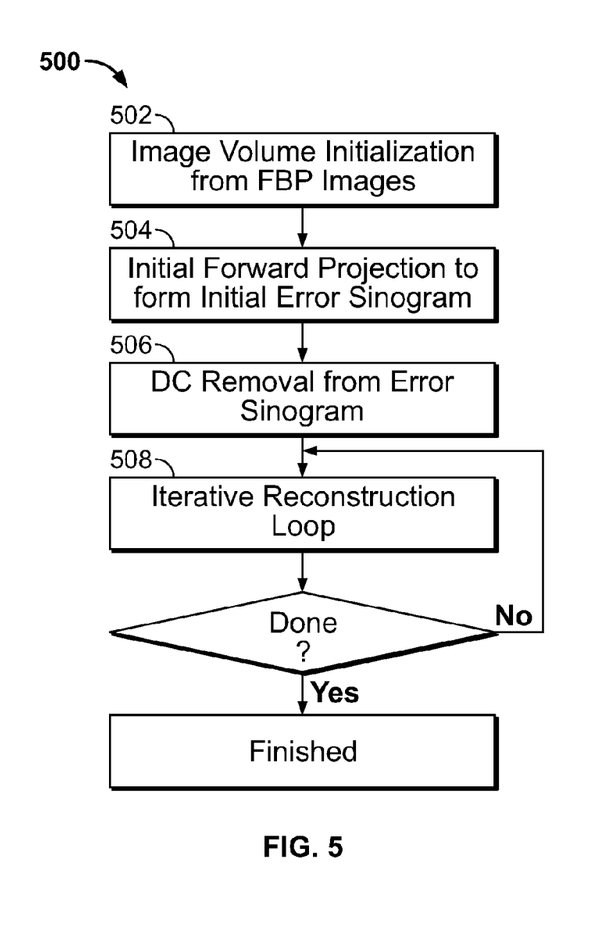
FIG. 5 is a flowchart of an exemplary method for correcting low-frequency shading artifacts in iterative reconstruction algorithms in accordance with an embodiment of the present invention.

FIG. 5 is a flowchart of an exemplary method 500 for the correction of low-frequency shading artifacts in iterative reconstruction algorithms in accordance with an embodiment of the present invention. Method 500 includes initialization 502 of the iterative algorithm with images reconstructed with for example, a direct reconstruction method such as but not limited to an FBP-like algorithm, a Katsevich-like algorithm or a Feldkamp-like algorithm. An initial forward projection 504 of the initial volume is performed to form the initial error sinogram. Elimination 506 of the DC component from the error sinogram. The DC component corresponds to the zero frequency. Therefore, eliminating it from the error sinogram ensures that the iterative reconstruction does not modify the DC component of the initial conditions. For example, FBP images void of low-frequency artifacts facilitate improving, iterative reconstruction image quality without introducing undesirable low-frequency artifacts.

In some cases, the initial conditions may provide only the information about a portion of the object. For instance, in cases where the object extends beyond the scan field of view, the portion of the object within the scan field of view may be reconstructed accurately with FBP, while the truncated portions may not be reconstructed at all, or only estimated with limited accuracy. The iterative reconstruction algorithm therefore will introduce DC information in the error sinogram at each step to reconstruct the full object, as the portions of the object outside the scan field of view converge.

The operation of DC component removal from the error sinogram may be performed using a least-squares estimation resulting in an additive correction. For example, an error sinogram is determined using:

$$e_i = y_i - \Sigma A_{ij} x_j, \quad (7)$$

where
y is the measured data, and
Ax is a forward projection of the estimated object x through the forward projection operator A.

$$\beta_i = \frac{\sum_{k \in S} w_k e_k}{\sum_{k \in S} w_k}, \text{ where} \quad (8)$$

β represents the mean of the projection errors for the ith view, w represents the weight associated with each measurement noise wherein the weight is inversely proportional to noise, The correction is applied according to:

$$e_i \leftarrow e_i - \beta_i, \quad (9)$$

where
the mean of the projection errors for each view are subtracted.

This operation can be performed either globally if S is the complete set of sinogram elements and equations (8) and (9) above are applied once over the whole sinogram, or the operation can be performed for each projection view and detector row pair if S is the set of elements in the view/row pair including i, and equations (8) and (9) above are repeated for each view/row pair. In one embodiment, the estimation of the coefficients β is a weighted sum, but it could also be performed without the weights, for example, $$\beta_i = \frac{1}{N_S} \sum_{k \in S} e_k,$$

where $N_S$ is the number of elements in the set S.

In another embodiment, DC component removal is performed using additional filtering similar to filtering used in FBP, for example, with a ramp filter or another high pass filter applied in the frequency domain over the Fourier transform of the error sinogram.

In still another embodiment, DC component removal is performed using another estimate of the correction coefficient $\beta_i$ calculated from the data, such as a maximum likelihood (ML) estimate. Equations (7), (8), and (9) above converge towards a joint ML/MAP estimate of β and x̂ using the quadratic likelihood approximation. Accordingly, the method provides for jointly estimating both the unknown gain or offset parameters and the reconstructed image during the iterative reconstruction process. The ML estimate is a natural generalization of the estimation proposed above when a Poisson counting noise model is considered to form the cost function.

In yet still another embodiment, the ML estimate of the unknown gain parameter is computed for each frame. If the conversion from counts to projections is modeled as a log operation, which is a common approximation, then these two things are the same. But if it isn't a perfect log operation, or if a more complex noise model is used, then the direct ML estimate of the gain parameter might be different.

Method 500 includes iteratively reconstructing 508 the image using the data with the DC component removed as described above. In the exemplary embodiment the iteration loops back without performing the DC component removal process again.

Figure 6:
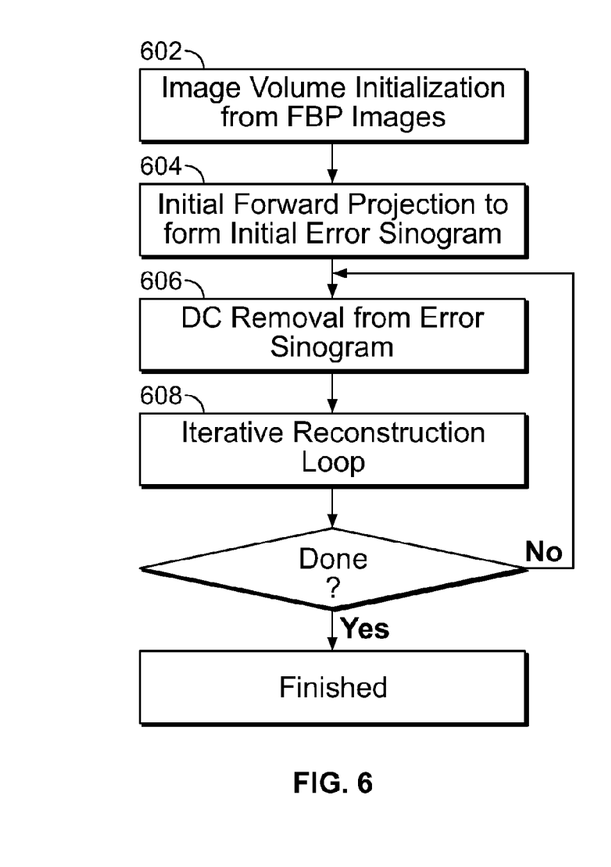
FIG. 6 is a flowchart of another exemplary method for correcting low-frequency shading artifacts in iterative reconstruction algorithms wherein the DC component removal step is performed inside the iterative loop.

FIG. 6 is a flowchart of another exemplary method 600 for the correction of low-frequency shading artifacts in iterative reconstruction algorithms wherein the DC component removal step is performed inside the iterative loop. When the DC component removal step is performed inside the iterative loop, the DC component is eliminated from the error sinogram at the beginning of each step, and the low-frequency content of the reconstructed images both inside and outside the scan field of view remains stable.

Method 600, similar to method 500 includes initialization 602 of the iterative algorithm with images reconstructed with a direct reconstruction type algorithm. An initial forward projection 604 of the initial volume is performed to form the initial error sinogram. The DC component from the error sinogram is eliminated 606 as described above. Method 600 also includes iteratively reconstructing 608 the image using the data with the DC component removed as described above. In the exemplary embodiment the iteration loops back and performs the DC component removal process prior to each iterative reconstruction step.

Figure 7A:
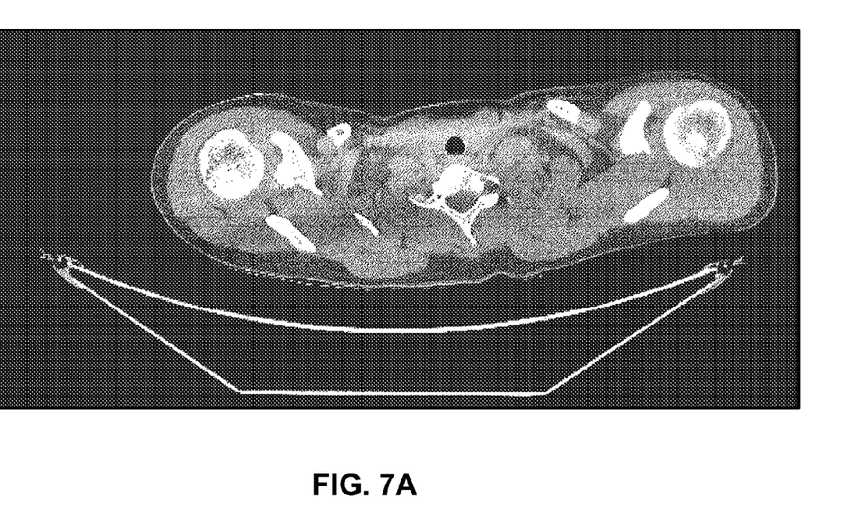
FIG. 7A is an uncorrected statistical iterative reconstruction image of the human shoulder patient shown in FIG. 3B.
Figure 7B:
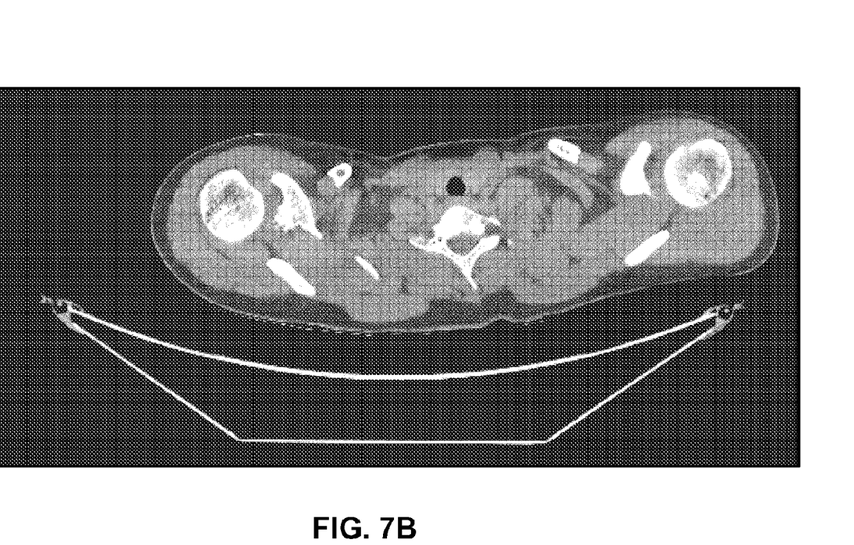
FIG. 7B is a statistical iterative reconstruction image of the human shoulder patient corrected by using weighted least-squares DC removal.

FIG. 7A is an uncorrected statistical iterative reconstruction image of the human shoulder patient (shown in FIG. 3B). FIG. 7B is a statistical iterative reconstruction image of the human shoulder patient corrected by using weighted least-squares DC removal. This correction facilitates elimination of low frequency artifacts in iterative reconstruction images. FIGS. 7A and 7B illustrate a comparison between the uncorrected image and the result of the correction applied inside the iterative loop on the shoulder patient. Dark shading artifacts are successfully corrected.

As will be appreciated by one skilled in the art and based on the foregoing specification, the above-described embodiments of the invention may be implemented using computer programming or engineering techniques including computer software, firmware, hardware or any combination or subset thereof, wherein the technical effect is to remove low-frequency truncation-related image artifacts in iterative reconstruction algorithms. Any such resulting program, having computer-readable code means, may be embodied or provided within one or more computer-readable media, thereby making a computer program product, i.e., an article of manufacture, according to the discussed embodiments of the invention. The computer readable media may be, for example, but is not limited to, a fixed (hard) drive, diskette, optical disk, magnetic tape, semiconductor memory such as read-only memory (ROM), and/or any transmitting/receiving medium such as the Internet or other communication network or link. The article of manufacture containing the computer code may be made and/or used by executing the code directly from one medium, by copying the code from one medium to another medium, or by transmitting the code over a network.

Although the methods described herein may be thought of as a removal of the DC component from the error state vector for iterative reconstruction, it is important to emphasize that we are performing estimation of gain and offset parameters in addition to image content, and nothing in this process prevents improvement in the DC content of the image from its initial state. Without special processing, truncated projections necessarily lead to FBP reconstructions with mass in projection data which is unrecovered in the image, and induce significant artifacts at the edge of the scan field-of-view where truncation occurs. Estimation of this truncated content facilitates high-quality iterative image estimates, where the reconstruction of all sources of measured x-ray attenuation is necessary to ensure consistency between the IR image and the projection data.

The above-described embodiments of an imaging system provide cost-effective and reliable systems and methods of eliminating low-frequency truncation-related image artifacts in iterative reconstruction algorithms. As a result, the described embodiments of the present invention facilitate imaging a patient in a cost-effective and reliable manner.

While the invention has been described in terms of various specific embodiments, those skilled in the art will recognize that the invention can be practiced with modification within the spirit and scope of the claims.

What is claimed is:

1. A method of tomographic image reconstruction comprising jointly estimating an estimation of the reconstructed image, and at least one of a gain parameter and an offset parameter.

2. A method in accordance with claim 1 comprising estimating multiplicative α gain factors wherein a represents the vector of unknown multiplicative gain factors applied to raw count measurements of the image data.

3. A method in accordance with claim 1 comprising estimating additive β offset factors wherein β is a vector of unknown additive offset factors applied to the integral projection measurements of the image data.

4. A method in accordance with claim 3 wherein estimating additive β offset factors comprises a joint estimation of the image values in x and the gain parameters in β wherein β represents a vector that of the unknown additive offset in the projection domain by taking the log of unknown multiplicative gains a in the counts domain, $\beta_i = \ln(\alpha_i)$.

5. A method in accordance with claim 1 comprising estimating multiplicative α gain factors and estimating additive β offset factors wherein α represents the vector of unknown multiplicative gain factors applied to raw count measurements of the image data and β is a vector of unknown additive offset factors applied to the integral projection measurements of the image data.

6. A method in accordance with claim 1 further comprising:
generating an error sinogram;
removing a zero frequency component from the error sinogram; and
reconstructing the image based at least in part on the error sinogram.

7. A method in accordance with claim 6 further comprising initializing an image volume based at least in part on a direct reconstruction image.

8. A method in accordance with claim 7 wherein generating an error sinogram comprises performing a forward projection of the direct reconstruction image.

9. A method in accordance with claim 6 wherein reconstructing the image comprises an iterative image reconstruction and wherein removing a zero frequency component from the error sinogram comprises removing the zero frequency component outside of the iterative reconstruction loop.

10. A method in accordance with claim 6 wherein reconstructing the image comprises an iterative image reconstruction and wherein removing a zero frequency component from the error sinogram comprises removing the zero frequency component inside of the iterative reconstruction loop.

11. A method in accordance with claim 6 wherein removing a zero frequency component from the error sinogram comprises removing the zero frequency component globally over the full error sinogram.

12. A method in accordance with claim 6 wherein removing a zero frequency component from the error sinogram comprises removing the zero frequency component for each row/view pair in the error sinogram.

13. A method in accordance with claim 6 wherein removing a zero frequency component from the error sinogram comprises weighting each projection coefficient with a value inversely proportional to the noise associated with that view.

14. A method in accordance with claim 6 wherein removing a zero frequency component from the error sinogram comprises correcting the error sinogram using an additive coefficient calculated by least-squares estimation.

15. A method in accordance with claim 6 wherein removing a zero frequency component from the error sinogram comprises correcting the error sinogram using filtering in the frequency domain.

16. A method in accordance with claim 6 wherein removing a zero frequency component from the error sinogram comprises correcting the error sinogram based at least in part on a Maximum Likelihood (ML) estimate of a correction coefficient.

17. A method in accordance with claim 16 wherein removing a zero frequency component from the error sinogram comprises jointly estimating the unknown gain parameters and the reconstructed image during the iterative reconstruction process.

18. A method in accordance with claim 16 wherein the ML estimate of an unknown gain parameter is calculated for each frame.

19. A method in accordance with claim 1 wherein image data is not normalized as a function of a detector reference channel measurement.

20. A method in accordance with claim 19 wherein image data is normalized as a function of an X-ray tube generator signal.

21. An imaging system comprising:
a database including information relating to tomographic data of an object to be imaged; and
a computer coupled to said database, said computer configured to perform a tomographic image reconstruction jointly as a function of an estimation of the reconstructed image, and at least one of an estimated gain parameter and an offset parameter.

22. A system in accordance with claim 21 wherein said computer is further configured to perform an iterative X-ray image reconstruction jointly as a function of an estimation of error correction gain parameters and an estimation of the reconstructed image.

23. A system in accordance with claim 21 wherein said computer is further configured to estimate multiplicative α gain factors wherein a represents the vector of unknown multiplicative gain factors applied to raw count measurements of the image data.

24. A system in accordance with claim 21 wherein said computer is further configured to estimate additive β offset factors wherein β is a vector of unknown additive offset factors applied to the integral projection measurements of the image data.

25. A system in accordance with claim 24 wherein said computer is further configured to estimate additive β offset factors comprises a joint estimation of the image values in x and the gain parameters in β wherein β represents a vector that of the unknown additive offset in the projection domain by taking the log of unknown multiplicative gains a in the counts domain, $\beta_i = \ln(\alpha_i)$.

26. A system in accordance with claim 21 wherein said computer is further configured to estimate multiplicative α gain factors and estimating additive β offset factors wherein α represents the vector of unknown multiplicative gain factors applied to raw count measurements of the image data and β is a vector of unknown additive offset factors applied to the integral projection measurements of the image data.

27. A system in accordance with claim 21 wherein said computer is further configured to:
- generate an error sinogram from a forward projection of a direct reconstruction of the image;
- remove a zero frequency component from the error sinogram; and
- iteratively reconstruct the image using based at least in part on the error sinogram.

28. A Computed Tomography (CT) System comprising:
- an X-ray source;
- a radiation detector; and
- a computer coupled to said X-ray source and said radiation detector, said computer configured to perform an X-ray image reconstruction jointly based at least in part on an estimated multiplicative $\alpha$ gain factor, an estimated additive $\beta$ offset factor, and an estimated reconstructed image wherein $\alpha$ represents the vector of unknown multiplicative gain factors applied to raw count measurements of the image data and $\beta$ is a vector of unknown additive offset factors applied to the integral projection measurements of the image data.

29. A non-transitory computer readable medium encoded with a program configured to instruct a computer to iteratively reconstruct a tomographic image jointly as a function of an estimation of the reconstructed image, and at least one of an estimation of error correction gain parameter and an estimation of error offset correction parameter.

30. A non-transitory computer readable medium in accordance with claim 29 is further configured to instruct a computer to estimate multiplicative $\alpha$ gain factors wherein $\alpha$ represents the vector of unknown multiplicative gain factors applied to raw count measurements of the image data.

31. A non-transitory computer readable medium in accordance with claim 29 is further configured to instruct a computer to estimate additive $\beta$ offset factors wherein $\beta$ is a vector of unknown additive offset factors applied to the integral projection measurements of the image data.

32. A non-transitory computer readable medium in accordance with claim 29 is further configured to instruct a computer to estimate additive $\beta$ offset factors comprises a joint estimation of the image values in x and the gain parameters in $\beta$ wherein $\beta$ represents a vector that of the unknown additive offset in the projection domain by taking the log of unknown multiplicative gains a in the counts domain, $\beta_i=\ln(\alpha_i)$.

33. A non-transitory computer readable medium in accordance with claim 29 is further configured to instruct a computer to estimate multiplicative $\alpha$ gain factors and estimating additive $\beta$ offset factors wherein $\alpha$ represents the vector of unknown multiplicative gain factors applied to raw count measurements of the image data and $\beta$ is a vector of unknown additive offset factors applied to the integral projection measurements of the image data.

34. A non-transitory computer readable medium in accordance with claim 29 is further configured to:
- generate an error sinogram from a forward projection of a direct reconstruction the image;
- remove a zero frequency component from the error sinogram; and
- iteratively reconstruct the image based at least in part on the error sinogram.

35. A non-transitory computer readable medium in accordance with claim 29 is further configured to remove a zero frequency component from the error sinogram via at least one of a weighted sum least squares estimation of an error correction coefficient, filtering using at least one of a ramp filter and a high pass filter applied in the frequency domain over a Fourier transform of the error sinogram, a maximum likelihood estimation of the error correction coefficient, a joint maximum likelihood estimation of the error correction coefficient and the reconstructed image, and a maximum likelihood estimation of the error correction coefficient for each reconstruction frame.

* * * * *